United States Patent [19]

Breitenbach et al.

[11] Patent Number: 5,731,009
[45] Date of Patent: Mar. 24, 1998

[54] IODOPHORE COMPOSED OF POLY-N-VINYLLACTAM AND DEXTRIN

[75] Inventors: Jörg Breitenbach, Linz; Axel Sanner, Frankenthal; Dietrich Thoma, Mannheim, all of Germany

[73] Assignee: BASF Aktiengesellschaft, Ludwigshafen, Germany

[21] Appl. No.: 727,667

[22] PCT Filed: Apr. 8, 1995

[86] PCT No.: PCT/EP95/01299

§ 371 Date: Oct. 17, 1996

§ 102(e) Date: Oct. 17, 1996

[87] PCT Pub. No.: WO95/28841

PCT Pub. Date: Nov. 2, 1995

[30] Foreign Application Priority Data

Apr. 23, 1994 [DE] Germany .................. 44 14 254.4

[51] Int. Cl.[6] .................. A61K 33/18; A61K 31/79
[52] U.S. Cl. .................. 424/672; 424/78.25; 514/778; 514/970
[58] Field of Search .................. 424/672, 78.25; 514/778, 970

[56] References Cited

U.S. PATENT DOCUMENTS

| | | | |
|---|---|---|---|
| 4,719,106 | 1/1988 | Shetty et al. | 424/80 |
| 4,844,898 | 7/1989 | Komori et al. | 424/672 |
| 5,455,042 | 10/1995 | Sakai et al. | 424/443 |

FOREIGN PATENT DOCUMENTS

| | | |
|---|---|---|
| 2074747 | 7/1992 | Canada . |
| 196813 | 10/1986 | European Pat. Off. . |
| 213717 | 3/1987 | European Pat. Off. . |
| 258761 | 3/1988 | European Pat. Off. . |
| 259 982 | 3/1988 | European Pat. Off. . |
| 380248 | 8/1990 | European Pat. Off. . |
| 526800 | 2/1993 | European Pat. Off. . |

*Primary Examiner*—John Pak
*Attorney, Agent, or Firm*—Keil & Weinkauf

[57] ABSTRACT

Iodophore containing a) 20–71% by weight of PVP or poly-N-vinylcaprolactam,
b) 20–71% by weight of dextrin of DE 2–40,
c) 6–25% by weight of elemental iodine,
d) 3–12.5% by weight of iodide ions, and process for its preparation are disclosed.

6 Claims, No Drawings

IODOPHORE COMPOSED OF POLY-N-VINYLLACTAM AND DEXTRIN

This application is a 371 of PCT/EP95/01299, filed on Apr. 8, 1995.

The present invention relates to an iodophore which has been improved in respect of properties and simplicity of preparation, where the carrier is composed of a mixture of dextrin with a poly-N-vinyllactam, namely poly-N-vinylpyrrolidone (PVP or polyvidone) or poly-N-vinylcaprolactam.

In the area of light-duty disinfectants, PVP-iodine is a long-established but cost-intensive product. Moreover, the preparation of saccharide-containing iodophores by polymerization of vinyl-pyrrolidone in the presence of the particular oligo- or polysac-charides is disclosed in EP-A 526 800. Although products of this type are less costly than PVP-iodine they do not meet the requirements of PVP-iodine. In addition, they have not hitherto received pharmacological acceptance.

EP-B 196 813 describes mixtures of PVP-iodine with sugar, EP-A 259 982 with sugar alcohols with and without sugar, EP-A 213 717 with sugar and a gelling polysaccharide. The preparation is complicated because it is necessary initially to prepare the PVP-iodine and then to mix it with the additive(s). Direct mixing of all the components is impossible. In addition, the products are unsuitable for pharmaceutical purposes because their available iodine content, the free iodine content and the iodine loss are, as a rule, outside the range permitted by the health authorities.

U.S. Pat. No. 4,719,106 describes mixtures of polydextrose-iodine and PVP-iodine. The preparation of polydextrose for this application is complicated and uneconomic: initially polysaccharides are decomposed to glucose, which is then polycondensed again in the presence of sorbitol and citric acid (cf. EP 380 248).

It is an object of the present invention to develop a simple and economic process for preparing an iodophore which meets the requirements of PVP-iodine in all respects.

We have found that this object is achieved by converting a mixture of PVP or poly-N-vinylcaprolactam and dextrin with a dextrose equivalent (DE) in the range from 2 to 40, preferably 10 to 30, into the iodine complex in a conventional way.

The dextrins are commercially available and can easily be obtained from starch by incomplete hydrolysis with dilute acid, by exposure to heat and by oxidative or enzymatic degradation with amylases.

Starch degradation products which can be obtained by hydrolysis in aqueous phase and have a weight average molecular weight of 2500 to 25,000 are normally called saccharified starches, to distinguish from the torrefaction dextrins, and are commercially obtainable as such.

Saccharified starches of this type differ chemically from the torrefaction dextrins inter alia by the fact that in a hydrolytic degradation in aqueous medium (normally suspensions or solutions), which is usually carried out at solids contents of 10–30% by weight and preferably with acid or enzyme catalysis, there is essentially no possibility of recombination and branching, which is also evident not least from the different molecular weight distributions.

The preparation of saccharified starches is generally known and described inter alia in Günther Tegge, Stärke und Stärkederivate, Behr's Verlag, Hamburg 1984, pages 173 and 220 et seq. and in EP-A 441 197. The saccharified starches to be used according to the invention are preferably those whose weight average molecular weight $M_w$ is in the range from 4000 to 16,000, particularly preferably in the range from 6500 to 13,000.

The saccharified starches to be used according to the invention are normally completely soluble in water at room temperature, the solubility limit usually being above 50% by weight. Preferably 10–20% by weight solutions, particularly preferably 30–40% by weight solutions, are clear and not colloidal suspensions at room temperature.

It is furthermore advisable to use according to the invention those saccharified starches which have a dextrose equivalent DE of 2–40, preferably 10–30, and particularly preferably 10–20. The DE characterizes the reducing capacity based on the reducing capacity of anhydrous dextrose and is determined by the DIN 10 308 method, Edition 5.71, of the Deutscher Normenausschuss Lebensmittel und landwirtschaftliche Produkte, (cf. also Günther Tegge, Stärke und Stärkederivate, Behr's Verlag, Hamburg 1984, p. 305).

Starches suitable as starting materials for preparing the saccharified starches to be used according to the invention are, in principle, all native starches such as cereals starches (eg. corn, wheat, rice or millet), tuber and root starches (eg. potatoes, cassava roots or arrowroot) or sago starches.

A considerable advantage of the saccharified starches to be used according to the invention is that no further chemical modification is required for their preparation for use, apart from the partial hydrolysis of the starch starting material which can be carried out in an extremely simple manner.

The saccharified starches used in the examples were the C* PUR products 01906, 01908, 01910, 01915, 01921, 01924, 01932 or 01934 of Cerestar Deutschland GmbH, Krefeld. Essentially all of them have a bimodal molecular weight distribution and have the following characteristics:

| Type | $M_w$ | H | % by weight <1000 | DE |
|---|---|---|---|---|
| 01906 | 20080 | 10.9 | 12.2 | 2–5 |
| 01908 | 19290 | 10.0 | 15.9 | 8–10 |
| 01910 | 10540–12640 | 8.5–9.9 | 24.7–26.4 | 11–14 |
| 01915 | 6680–8350 | 6.8–8.4 | 32.9–34.7 | 17–19 |
| 01921 | 6700 | 7.4 | 39.1 | 20–23 |
| 01924 | 4730 | 6.8 | 53.6 | 26–30 |
| 01932 | 4500 | 7.9 | 63.2 | 33–35 |
| 01934 | 3000 | 6.0 | 68.4 | 36–39 |

Determinations of $M_n$ by vapor pressure osmosis yielded the following values for the preferred types 01910 and 01915: 1560 g/mol (1910) 980 g/mol (1915)
H = Heterogeneity
$M_w$ = weight average molecular weight
$M_n$ = Number average molecular weight
DE = Dextrose equivalent For the reaction of the iodine and iodide with the carrier in the solid state it is necessary for the carrier to be homogeneous. This homogeneity can be achieved by drying the solution of all the components, but it is also sufficient to grind the powdered components thoroughly together. This can take place by conventional techniques, eg. with ball mills, intensive mixers, tumble mixers with balls etc. Iodine and reducing agent or iodide can subsequently be admixed as solid or solution in the same vessel. The complexes formed by adding sufficient iodine and iodide for the final mixture to contain 6–25, preferably 15–20%, by weight of iodine and 1 mole of iodide per mole of iodine ($I_2$), and subsequently heating at 50°–110° C. for several hours. Any cation is suitable for the iodide, usually sodium or potassium. The iodide can be replaced by an equivalent amount of an agent which reduces iodine to iodide, for example formic acid and its salts, preferably ammonium formate, glucose, ascorbic acid, malonic acid, oxalic acid, ammonium oxalate, urea, urea-$H_2O_2$, or ammonium carbamate, if the initial amount of iodine is increased correspondingly. Account must also be taken of the fact that dextrins have, because of their aldehydic end groups, a certain capacity to reduce iodine.

The complete mixture can, if in the form of a solution (preferably in water), be marketed and used in this form. However, the iodophores are usually prepared and marketed in powder form. They can be used as light-duty disinfectants likewise in powder form or in aqueous solution. In any event, the action starts only in solution and it is thus necessary on dry application for at least moisture to be present in some form (eg. wound discharge on medical use). The iodophore can also be incorporated and used in creams, aerosols or forms such as suppositories.

The contents by weight in the complete mixture (based on the solids content in the case of a solution) are 20–71, preferably 30–60%, PVP or poly-N-vinylcaprolactam, 20–71, preferably 30–60%, dextrin, 9–37.5% iodine, of which one third is in each case in the form of iodide ions, and 0–900, preferably 0–500, % water.

The polymeric vinyllactams have K values determined by the method of H. Fikentscher (Cellulosechemie 13 (1932), 58–64 and 71–74) in the range from 12 to 100, preferably 25 to 70. Crosslinked PVP can also be used to prepare solid iodophore and can be reacted with starches which are insoluble in water to give an iodine complex and thus be used, for example, for application to wounds.

The available iodine content is determined by the method in the Deutscher Arzneimittel Codex (DAC) 1986, 2nd Supplement 1990, for polyvidone-iodine. The content specified therein is from a minimum of 9 and a maximum of 12% available iodine. The same applies to USP XXII (povidone-iodine), which also describes the determination of the iodide content. The available iodine content corresponds to the value measured by titration against thiosulfate. The free iodine content is determined by the method of D. Horn and W. Ditter "PVP-Iod in der operativen Medizin", pages 7 et seq., Springer-Verlag, Heidelberg 1984.

The total weight loss on drying in an oven at 100°–105° C. (loss on drying) is also fixed in the DAC 1986, 3rd part 1988, at a maximum of 8% on 0.5 g of substance, and the products according to the invention comply with this.

The loss of available iodine (iodine loss) on storage at elevated temperature gives information about the stability of the complex and is determined as follows:

The determination is carried out on a PVP-iodine solution which contains 1% available iodine. This is prepared as follows: x g of PVP-iodine sample are weighed into a 100 ml Erlenmeyer flask with stopper and made up to a total weight of 50 g with water.

Calculation of the amount x in grams to be weighed in:

$$x = \frac{5000}{(100 - LD) \times AI}$$

LD=% loss on drying (DAC method)
AI=% available iodine (DAC method)
The solution is shaken for 3 hours.

After shaking, 5.0 ml are pipetted with a calibrated bulb pipette into a 250 ml Erlenmeyer flask, diluted with—100 ml of distilled water and 1 drop of acetic acid and titrated against 0.02N sodium thiosulfate solution as quickly as possible to the end-point (colorless or pale yellow color) (V used).

Storage at elevated temperature

A brown 25 ml bottle with stopper is filled to 1 cm below the stopper with PVP-iodine solution and subsequently stored in an oven at 80°±0.5° C. for 15 hours. The bottle is briefly vented by lifting the stopper about 15 minutes after introduction into the oven. After storage for 15 hours and after cooling of the bottle contents, 5.0 ml are removed, and the available iodine content is determined as described in the DAC with 0.02N sodium thiosulfate solution (N used).

Calculation of the iodine loss $$\% \text{ iodine loss} = \frac{V - N}{V} \cdot 100$$

where:

V=ml of $Na_2S_2O_3$ solution used before storage
N=ml of $Na_2S_2O_3$ solution used after storage
Note:

In order to be able to detect irregularities (temperature fluctuations, current failure etc) during storage it is expedient also to analyze a comparative sample with known iodine loss.

The dextrins on their own are unable to form sufficiently stable iodine complexes. Surprisingly, however, they are able to when mixed with PVP or poly-N-vinylcaprolactam since equal amounts of the mixture, on the one hand, and of unmixed PVP or poly-N-vinyl-caprolactam, on the other hand, take up identical amounts of iodine with the same binding power. There is thus evidently a type of synergism in the mixture. In contrast to graft copolymers, the mixtures are pharmacologically acceptable products. Compared with PVP-iodine, the iodophores according to the invention not only have ecological advantages based on the good biodegradability of the dextrin content but also have economic advantages because the starting material costs are greatly reduced. In addition, the iodophores according to the invention surprisingly, in contrast to the known ones with different (poly)saccharides, usually comply in all points with the requirements of the approval regulations and of practice, as the following table shows:

Comparison between PVP-dextrin-iodine according to the invention and other PVP-polysaccharide-iodine adducts

|  | | Available iodine content (DAC) % | Iodine loss % | Free iodine ppm | Iodide (DAC) % |
|---|---|---|---|---|---|
| Pharmacologically acceptable or desired range | | 9–12 | 1–5 | 3–6 | ≦6 |
| Example 1 | | 11.7 | 2.6 | 3.0 | 5.3 |
| Example 2 | | 12.0 | 1.5 | 2.6 | 4.7 |
| Example 3 | | 10.7 | 3.0 | 3.0 | 5.9 |
| Example 4 | | 11.3 | 2.5 | 3.0 | 5.6 |
| Example 5 | | 10.8 | 4.0 | 2.5 | 6.0 |
| Example 6 | | 11.9 | 3.3 | 3.2 | 4.9 |
| Example 7 | | 11.5 | 1.6 | 1.5 | 5.9 |
| Example 8 | | 11.8 | 1.6 | 5.0 | 5.0 |
| Example 9 | | 10.1 | 1.7 | 5.9 | 4.7 |
| Comp. Ex. 1 | PVP-starch (Zulkowsky*)-iodine | 10.6 | 7.4 | 10 | 17.5 |
| Comp. Ex. 2 | α-D-Glucose-PVP-iodine | 13.1 | 28.3 | 50 | — |
| Comp. Ex. 3 | Sucrose-PVP-iodine | 13.2 | 15.7 | 30 | — |
| Comp. Ex. 4 | α-Cyclodextrin-PVP-iodine | 10.8 | 41.0 | — | — |
| Comp. Ex. 5 | β-Cyclodextrin-PVP-iodine | 12.3 | precipitation | — | — |
| Comp. Ex. 6 | γ-Cyclodextrin- | 13.4 | precip- | | |

| Comparison between PVP-dextrin-iodine according to the invention and other PVP-polysaccharide-iodine adducts | | | |
|---|---|---|---|
| | Available iodine content (DAC) % | Iodine loss % | Free iodine ppm | Iodide (DAC) % |
| PVP-iodine | | itation | |

*K. Zulkowsky, Ber. d. Deutschen Chem. Ges. 18 (1980), 1395.

Since the previously disclosed extenders for PVP-iodine, namely sugars, sugar alcohols and gel-forming polysaccharides, as well as the costly polydextrose, have not provided a satisfactory solution by not complying with drug approval regulations, it was not expected that the industrially simpler solution according to the invention could provide better results. The invention thus provides, in a surprisingly simple manner, novel iodophores which are of lower cost than PVP-iodine and technically at least equivalent.

EXAMPLES

1. A mixture of equal parts by weight of dextrin with a DE of 17.5–19 and polyvinylpyrrolidone (K=30) was mixed with 1.5% ammonium formate and 17% iodine, based on the polymer content, in a mixer, initially at room temperature for 1 h and then at 70° C. for 20 h. The solids content of the powder was 95.8%, the available iodine content was 11.7%, the iodine loss was 2.6%, the free iodine content was 3.0 ppm and the iodide content was 5.3%.

2. A mixture of equal parts of dextrin with a DE of 17.5–19 and popolyvinylpyrrolidone (K=30) was mixed with 1.5% ammonium formate and 17% iodine, based on the polymer content, in a mixer, initially at room temperature for 1 h and then at 80° C. for 8 h. The solids content of the powder was 97.0%, the available iodine content was 12.0%, the iodine loss was 1.5%, the free iodine content was 2.6 ppm and the iodide content was 4.7%.

3. A mixture of equal parts of dextrin with a DE of 13 and poly-vinylpyrrolidone (K=30) was mixed with 1.5% ammonium formate and 17% iodine, based on the polymer content, in a mixer, initially at room temperature for 1 h and then at 70° C. for 20 h. The solids content of the powder was 96.8%, the available iodine content was 10.7%, the iodine loss was 3.0%, the free iodine content was 3 ppm and the iodide content was 5.9%.

4. A mixture of equal parts of dextrin with a DE of 10 and poly-vinylpyrrolidone (K=30) was mixed with 1.5% ammonium formate and 17% iodine, based on the polymer content, in a mixer, initially at room temperature for 1 h and then at 80° C. for 8 h. The solids content of the powder was 96.5%, the available iodine content was 11.3%, the iodine loss was 2.5%, the free iodine content was 3 ppm and the iodide content was 5.6%.

5. A solution of equal parts of dextrin with a DE of 10 and polyvinylpyrrolidone (K=30) was mixed with 1.5% formic acid and spray dried. Subsequently 15% iodine was added and the powder was mixed at room temperature for 1 h and at 70° C. for 20 h. The product had a solids content of 96.5%, the available iodine content was 10.8%, the iodine loss was 4%, the free iodine content was 2.5 ppm and the iodide content was 6.0%.

6. A mixture of dextrin with a DE of 17.5–19 and polyvinylpyrrolidone (K=30) in the ratio 1.25:1 by weight was mixed with 1.5% ammonium formate and 17% iodine, based on the polymer content, in a mixer, initially at room temperature for 1 h and then at 80° C. for 9 h. The solids content of the powder was 95.0%, the available iodine content was 11.9%, the iodine loss was 3.3%, the free iodine content was 3.2 ppm and the iodide content was 4.9%.

7. A mixture of dextrin with a DE of 17.5–19 and polyvinylpyrrolidone (K=60) in the ratio 1.5:1 was mixed with 1.5% ammonium formate and 17% iodine, based on the polymer content, in a mixer, initially at room temperature for 2 h and then at 80° C. for 8 h. The solids content of the powder was 95.6%, the available iodine content was 11.5%, the iodine loss was 1.6%, the free iodine content was 1.5 ppm and the iodide content was 5.9%.

8. A mixture of dextrin with a DE of 17.5–19 and polyvinylpyrrolidone (K=30) in the ratio 2:1 was mixed with 1.5% ammonium formate and 17% iodine, based on the polymer content, in a mixer, initially at room temperature for 2 h and then at 80° C. for 8 h. The solids content of the powder was 94.9%, the available iodine content was 11.8%, the iodine loss was 1.6%, the free iodine content was 5 ppm and the iodide content was 5%.

9. A mixture of dextrin with a DE of 17.5–19 and polyvinylcaprolactam (K=32) in the ratio 1:1 was mixed with 1% ammonium formate and 15% iodine, based on the polymer content, in a mixer, initially at room temperature for 1 h and then at 90° C. for 8 h. The solids content of the powder was 96%, the available iodine content was 10.1%, the iodine loss was 1.7 the free iodine content was 5.9 ppm and the iodide content was 4.7%.

We claim:

1. An iodophore comprising
   a) 20–71% by weight of PVP or poly-N-vinylcaprolactam,
   b) 20–71% by weight of saccharified starch of DE 2–40,
   c) 6–25% by weight of elemental iodine,
   d) 3–12.5% by weight of iodide ions,
   which iodophore is prepared by a process selected from the group consisting of:
   (i) mixing powdered components of (a) to (d), or mixing powdered components of (a), (b), and sufficient amount of powdered elemental iodine and a reducing agent to provide (c) 6–25% by weight of elemental iodine and (d) 3–12.5% by weight iodide ions, and heating the mixture at 50°–110° C. for 3–30 hours;
   (ii) heating a solution of (a) to (d), or heating a solution of (a), (b), and sufficient amount of elemental iodine and a reducing agent to provide (c) 6–25% by weight of elemental iodine and (d) 3–12.5% by weight iodide ions, at 50°–100° C. for 3–30 hours; and
   (iii) dissolving components (a) and (b) in minimal amount of water, spray-drying the solution, mixing the resulting powder with powdered components (c) and (d), or dissolving components (a) and (b) in minimal amount of water, spray-drying the solution, mixing the resulting powder with sufficient amount of powdered elemental iodine and a reducing agent to provide (c) 6–25% by weight of elemental iodine and (d) 3–12.5% by weight iodide ions, and heating the mixture at 50°–90° C. for 3–30 hours.

2. A liquid iodophore composed of a 0.1–40% by weight strength aqueous solution of an iodophore as claimed in claim 1.

3. An iodophore as claimed in claim 1, wherein the saccharified starch has a DE of 10–30.

4. A process for preparing an iodophore as claimed in claim 1 comprising mixing powdered components (a) to (d), or mixing powdered components of (a), (b), and sufficient amount of powdered elemental iodine and a reducing agent to provide (c) 6–25% by weight of elemental iodine and (d) 3–12.5% by weight iodide ions, and heating the mixture at 50°–110° C. for 3–30 hours.

5. A process for preparing an iodophore as claimed in claim 1 comprising heating a solution of components (a) to (d) together, or heating a solution of (a), (b), and sufficient amount of elemental iodine and a reducing agent to provide (c) 6–25% by weight of elemental iodine and (d) 3–12.5% by weight iodide ions, at 50°–100° C. for 3–30 hours.

6. A process for preparing an idophore as claimed in claim 1 comprising dissolving components (a) and (b) in minimal amount of water, spray-drying the solution, mixing the resulting powder with powdered components (c) and (d), or dissolving components (a) and (b) in minimal amount of water, spray-drying the solution, mixing the resulting powder with sufficient amount of powdered elemental iodine and a reducing agent to provide (c) 6–25% by weight of elemental iodine and (d) 3–12.5% by weight iodide ions, and heating the mixture at 50°–90° C. for 3–30 hours.

* * * * *

UNITED STATES PATENT AND TRADEMARK OFFICE
CERTIFICATE OF CORRECTION

PATENT NO.: 5,731,009

DATED: March 24, 1998

INVENTOR(S): BREITENBACH et al.

It is certified that error appears in the above-identified patent and that said Letters Patent is hereby corrected as shown below:

Column 8, claim 1, line 1, "idophore" should be --iodophore--.

Signed and Sealed this

Nineteenth Day of May, 1998

*Attest:*

BRUCE LEHMAN

*Attesting Officer*     *Commissioner of Patents and Trademarks*